(12) United States Patent
Pawliszyn et al.

(10) Patent No.: US 8,104,331 B2
(45) Date of Patent: Jan. 31, 2012

(54) METHOD AND DEVICE TO EXTRACT COMPONENTS CONTAINED IN A FLUID

(75) Inventors: Janusz Pawliszyn, Waterloo (CA); Marcel Musteata, Waterloo (CA); Ines Ana Maria De Lannoy, Toronto (CA); Kenneth Bradley Gien, Brantford (CA)

(73) Assignees: Noab Biodiscoveries Inc., Mississauga (CA); Janusz Pawliszyn, Waterloo (CA)

( * ) Notice: Subject to any disclaimer, the term of this patent is extended or adjusted under 35 U.S.C. 154(b) by 472 days.

(21) Appl. No.: 12/374,058

(22) PCT Filed: Jul. 19, 2007

(86) PCT No.: PCT/CA2007/001275
§ 371 (c)(1),
(2), (4) Date: Jan. 16, 2009

(87) PCT Pub. No.: WO2008/009120
PCT Pub. Date: Jan. 24, 2008

(65) Prior Publication Data
US 2010/0011888 A1  Jan. 21, 2010

Related U.S. Application Data

(60) Provisional application No. 60/831,567, filed on Jul. 19, 2006.

(51) Int. Cl.
*G01N 1/14* (2006.01)
(52) U.S. Cl. .................. 73/64.56; 73/863.81; 73/863.83; 73/863.85
(58) Field of Classification Search .................. 73/64.56, 73/863.85, 863.83, 864.15, 864.16
See application file for complete search history.

(56) References Cited

U.S. PATENT DOCUMENTS

| | | | | |
|---|---|---|---|---|
| 3,991,627 A | * | 11/1976 | Laird et al. | 73/864.16 |
| 4,231,366 A | | 11/1980 | Schael | |
| 4,796,644 A | | 1/1989 | Polaschegg | |
| 5,691,206 A | * | 11/1997 | Pawliszyn | 436/178 |
| 6,099,470 A | * | 8/2000 | Bahr | 600/366 |
| 6,537,827 B1 | | 3/2003 | Pawliszyn | |
| 6,736,783 B2 | | 5/2004 | Blake et al. | |
| 2004/0047768 A1 | * | 3/2004 | Sullivan | 422/100 |

OTHER PUBLICATIONS

Yongxin Zhu, et al., "How a Rodent is Dosed and Sampled is Equally Important to How Samples are Analyzed: Automated Dosing, Sampling and LC/MSMS with Ion Traps and Triple Quads", Bioanalytical Systems Inc., vol. 21, No. 5, Aug. 2005, pp. 37-44.

\* cited by examiner

*Primary Examiner* — Hezron E Williams
*Assistant Examiner* — Paul West
(74) *Attorney, Agent, or Firm* — Bereskin & Parr LLP/S.E.N.C.R.L., s.r.l.

(57) ABSTRACT

Applicants' teachings relate to a method and device to extract components contained in a fluid. More particularly, the applicants' teachings are directed towards a method and sampling device for quick extraction of targeted components from their in vivo surroundings. In accordance with various embodiments of applicants' teachings a sampling device and method to extract components, such as, for example, analytes, from a fluid is provided. The device is interfaced with a fluid source, such as, for example, but not limited to, a circulatory system of an animal, to enable extraction of target molecules with minimal loss of fluid (e.g., blood) to the source. The device facilitates an interface between the circulatory system of an animal and a suitable sampling probe such as, for example, a solid phase microextraction (SPME) probe. The targeted compounds are desorbed in small volumes of solvents that can be analyzed with highly specific instruments.

11 Claims, 12 Drawing Sheets

METHOD AND DEVICE TO EXTRACT COMPONENTS CONTAINED IN A FLUID

This application is a National Stage of International Application No. PCT/CA2007/001275 which claims the benefit of U.S. Provisional Application No. 60/831,567, filed Jul. 19, 2006, the entire contents of which is hereby incorporated by reference.

The section headings used herein are for organizational purposes only and are not to be construed as limiting the subject matter described in any way.

FIELD

Applicants' teachings relate to a method and device to extract components contained in a fluid. More particularly, the applicants' teachings are directed towards a method and sampling device for quick extraction of targeted components from their in vivo surroundings.

INTRODUCTION

To study a drug's pharmacokinetic (PK) profile in an animal model, the drug is administered by the desired route of administration, followed by sampling and analysis of a biological fluid, such as whole blood or plasma. In order to obtain reproducible and good quality data, the sampling method is as important as the method of bioanalysis. For example, animals that experience stress during sampling can exhibit altered PK profiles (Zhu et al., 2005, Current Separations 21, 37-44; Barton, 2005, J Toxicol Environ Health A 68, 889-900).

Currently, many PK studies in rodents require either a large number of animals because they are performed by sacrificing several rodents for each data point (Gueorguieva et al. 2004, J Pharmacokinet Pharmacodyn 31, 185-213; Corley et al., 2005, Toxicol Sci 85, 476-490; Anderton. et al., 2004, Clin Cancer Res 10, 5233-5241; Scott-Stevens et al., 2005, Biopharm Drug Dispos 26, 13-20) or a fewer number of catheterized animals, when the blood sample volume is usually replaced (Valenzano et al., 2005, Neuropharmacology 48, 658-672).

In the absence of blood volume replacement, the number of samples that can be taken is limited as serious hemorrhagic shock and tissue anoxia can occur if more than 20% of the total blood volume is drawn. This can be ameliorated by replacing the sample volume with blood obtained from a donor animal. However, this introduces sample dilution and involves the sacrifice of more animals. Methods such as microdialysis and ultrafiltration do not require blood draws and are suitable for automation, but they are not appropriate for drugs highly bound to plasma proteins and have difficulty producing accurate quantitative results (Kennedy et al., 2002, J Neurosci Methods 114, 39-49; Leegsma-Vogt et al. Life Sci 73, 2005-2018). Further, sensors and sensor arrays are usually very small and have a short response time but they are very difficult to produce and may not be suitable for complex biological samples (Walt, 2005, 308, 217-219).

SUMMARY

Applicants' teachings relate to a method and device to extract components contained in a fluid. More particularly, the applicants' teachings are directed towards a method and sampling device for quick extraction of targeted components from their in vivo surroundings.

In accordance with various embodiments of applicants' teachings a sampling device and method to extract components, such as, for example, analytes, from a fluid is provided. The device is interfaced with a fluid source, such as, for example, but not limited to, a circulatory system of an animal, to enable extraction of target molecules with minimal loss of fluid (e.g., blood) to the source. The device facilitates an interface between the circulatory system of an animal and a suitable sampling probe such as, for example, a solid phase microextraction (SPME) probe. The targeted compounds are desorbed in small volumes of solvents that can be analyzed with highly specific instruments.

In particular, in various embodiments of applicant's teachings a device to extract components contained in a fluid is provided. The device comprises a housing defining a cavity, with the housing having at least one opening to allow fluid flow into and out of the cavity. The device also comprises a probe insertable into the cavity of the housing. Moreover, the device comprises a channel, with the channel adapted to connect the cavity to a fluid pump, so that when the probe is inserted into the cavity the fluid pump causes fluid to flow into and out of the cavity through the at least one opening and contact the probe in the cavity.

In accordance with some embodiments of applicant's teachings, the probe comprises, for example, a solid phase microextraction apparatus.

Moreover, in accordance with some embodiments of applicant's teachings the at least one opening comprises, for example, but not limited to, a catheter or a cannula.

In accordance with some embodiments of applicant's teachings, the at least one opening is one opening and the fluid flows into and out of the cavity through such one opening.

Alternatively, in accordance with some embodiments of applicant's teachings, the fluid flows into the cavity through one of the opening or channel, and the fluid flows out of the cavity through the other of the opening or channel.

Further, in accordance with various embodiments of applicant's teachings the channel comprises a luer lock, and the luer lock is adapted to connect a fluid pump to the channel.

In accordance with various embodiments of applicant's teachings the device further comprises a fluid pump connected to the channel to cause fluid to flow into and out of the cavity. In accordance with some embodiments of applicant's teachings, the device is a connected to a circulatory system of a live animal or human, and the circulatory system acts as a fluid pump to cause fluid to flow into and out of the cavity.

In some embodiments of applicant's teachings, the fluid pump is, for example, but not limited to, a syringe, and the push/pull action of the syringe causes fluid to flow into and out of the cavity.

In accordance with various embodiments of applicant's teachings at least one of a wall that defines the cavity is adapted to sealingly receive therethrough at least a portion of the probe. In some embodiments of applicant's teachings, such wall of the cavity comprises, for example, but not limited to, a septum.

In some embodiments of applicant's teachings, the probe can comprise a needle adapted to pierce the septum. Similarly, in some embodiments of applicant's teachings, the syringe can comprise a needle, and the needle of the syringe is adapted to pierce the septum.

According to the various embodiments of applicant's teachings, the SPME probe comprises a fiber extendable into the cavity to extract components, such as, for example, analytes, from the fluid received in the cavity. In some embodiments of applicant's teachings the source of fluid is a live animal or human. In more specific embodiments, the live animal is, for example, but not limited to, a rodent, rabbit, dog, pig, monkey, mouse, rat, or guinea pig.

Inside the cavity, the fluid contacts the sampling probe, such as for example, a retractable SPME fiber. The SPME fiber can be extended into the cavity to extract target components from the fluid, and then be retracted from the cavity and device for analysis.

In accordance with various embodiments of applicant's teachings, a method of extracting components contained in a fluid is disclosed. The method comprises placing a housing defining a cavity in fluid contact with a source of fluid having components to be extracted therefrom, inserting at least a portion of a probe to extract the components contained in the fluid into the cavity of the housing, drawing fluid from the source of fluid into the cavity so that when the probe is inserted into the cavity the fluid contacts at least a portion of the probe, and returning the fluid from the cavity to the source of fluid after fluid has been in contact with the probe.

In accordance with some embodiments of applicant's teachings, the probe comprises, for example, a solid phase microextraction apparatus.

Moreover, in accordance with some embodiments of applicant's teachings the fluid is in contact with the at least a portion of the probe for a predetermined amount of time.

Further, in accordance with some embodiments of applicant's teachings the fluid flow can be caused by the circulatory system of a live animal or human, or can be, for example, controlled by a fluid pump. The fluid pump can be, for example, but not limited to, a syringe.

In accordance with some embodiments of applicant's teachings, the fluid flows into and out of the cavity through the same fluid flow path between the cavity and the source of fluid. In accordance with some embodiments of applicant's teachings, a second fluid flow path is provided so that fluid is drawn from the source of fluid into the cavity through one of the fluid flow paths to contact at least a portion of the probe, and the fluid is returned to the source of fluid through the other of the fluid flow paths.

In accordance with various embodiments of applicant's teachings, the probe is removed from the cavity after the fluid contacts at least a portion of the probe, and the components analyzed.

In accordance with various embodiments of applicant's teachings, the method can be used for live animals or humans. The live animals can be, for example, but not limited to, rodent, rabbit, dog, pig, monkey, mouse, rat or guinea pig.

In accordance with various embodiments of applicant's teachings, use of a device as described above to extract components contained in a fluid is provided. The use comprises placing the housing of the device in fluid contact with a source of fluid having components to be extracted therefrom, inserting at least a portion of the probe to extract the components contained in the fluid into the cavity of the housing, drawing fluid from the source of fluid into the cavity so that when the probe is inserted into the cavity the fluid contacts at least a portion of the probe, and returning the fluid from the cavity to the source of fluid after fluid has been in contact with the probe.

In accordance with some embodiments of the use of the device of applicant's teachings, the probe comprises, for example, a solid phase microextraction apparatus.

Moreover, in some embodiments of the use of the device according to applicant's teachings the fluid is in contact with the at least a portion of the probe for a predetermined amount of time.

Further, in accordance with some embodiments of the use of the device of applicant's teachings the fluid flow can be caused by the circulatory system of a live animal or human, or can be, for example, controlled by a fluid pump. The fluid pump can be, for example, but not limited to, a syringe.

In accordance with some embodiments of the use of the device of applicant's teachings, the fluid flows into and out of the cavity through the same fluid flow path between the cavity and the source of fluid. In accordance with some embodiments of applicant's teachings, a second fluid flow path is provided so that fluid is drawn from the source of fluid into the cavity through one of the fluid flow paths to contact at least a portion of the probe, and the fluid is returned to the source of fluid through the other of the fluid flow paths.

In accordance with various embodiments of the use of the device of applicant's teachings, the probe is removed from the cavity after the fluid contacts at least a portion of the probe, and the components analyzed.

Further, in accordance with various embodiments of the use of the device of applicant's teachings, the device can be used on live animals or humans. The live animals can be, for example, but not limited to, rodent, rabbit, dog, pig, monkey, mouse, rat or guinea pig.

Further, in accordance with various embodiments of applicant's teachings, a kit for use in carrying out a method as defined above is provided. The kit comprises a device having a housing defining a cavity, the housing having at least one opening to allow fluid flow into and out of the cavity, and a probe adapted to be insertable into the cavity of the housing.

In accordance with some embodiments of the kit of applicant's teachings, the probe comprises a solid phase microextraction apparatus.

In accordance with some embodiments of the kit of applicant's teachings, the kit further comprising a fluid pump, the fluid pump adapted to cause fluid to flow into and out of the cavity. In some embodiments, the fluid pump can comprise, for example, but not limited to, a syringe.

In accordance with some embodiments of the kit of applicant's teachings, the fluid pump is connected to the cavity by a luer lock.

In accordance with some embodiments of the kit of applicant's teachings, the at least one opening can comprise, for example, but not limited to, a catheter or a cannula.

In accordance with some embodiments of the kit of applicant's teachings, the at least one opening is one opening and the fluid flows into and out of the cavity through such one opening.

In accordance with some embodiments of the kit of applicant's teachings, the fluid flows into the cavity through one of the opening or channel, and the fluid flows out of the cavity through the other of the opening or channel.

These and other features of the applicant's teachings are set forth herein.

DRAWINGS

The skilled person in the art will understand that the drawings, described below, are for illustration purposes only. The drawings are not intended to limit the scope of the applicant's teachings in any way.

DESCRIPTION OF VARIOUS EMBODIMENTS

Figure 1A:
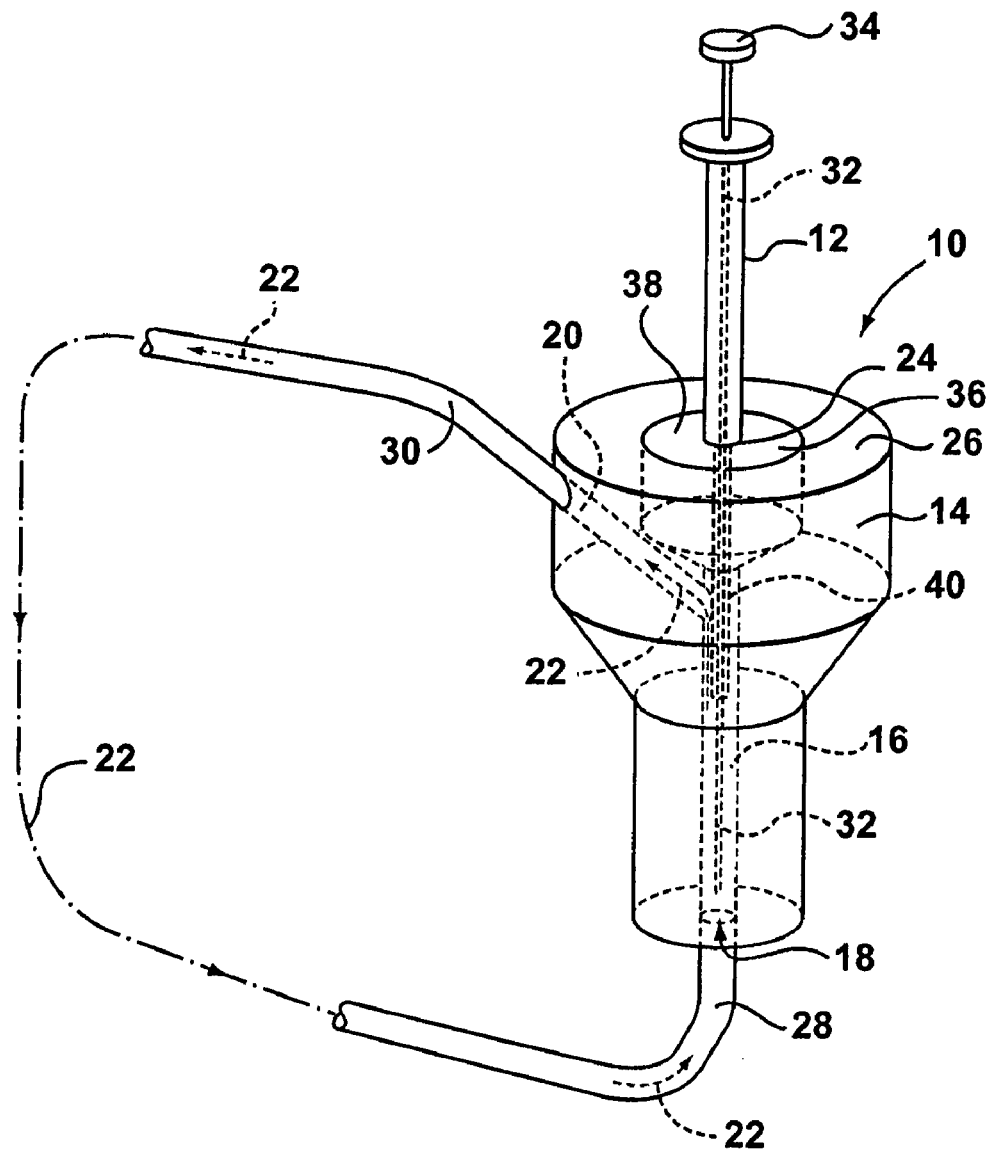
FIG. 1a is a perspective view of some embodiments of the device of applicant's teachings.

In accordance with various embodiments of applicants' teachings a sampling device 10 to extract components, such as, for example, analytes, from a fluid is illustrated in FIG. 1a. The device is interfaced with a fluid source, such as, for example, but not limited to, a circulatory system of an animal (not illustrated), to enable extraction of target molecules with minimal loss of fluid (e.g., blood) to the source. The device 10 facilitates an interface between the circulatory system of the animal and a suitable sampling probe 12 such as, for example, a solid phase microextraction (SPME) probe. The targeted compounds are desorbed in small volumes of solvents that can be analyzed with highly specific instruments.

As illustrated in FIG. 1a, the device 10 comprises a housing 14 defining a cavity 16. The housing 14 has at least one opening 18 to allow fluid flow into and out of the cavity 16. For the device 10 illustrated in FIG. 1a, two openings are provided, namely, opening 18 and a channel 20 that allow fluid to flow through the cavity 16 in the direction of arrows 22. For the embodiments illustrated, the probe 12 is insertable into the cavity 16 of the housing 14 through an opening 24 in the top surface 26 of the housing 14.

In accordance with various embodiments of applicant's teachings the device 10 is a connected to a circulatory system of a live animal or human, and the circulatory system acts as a fluid pump to cause fluid to flow in the direction of arrows 22 into the cavity 16 through opening 18, and out of the cavity 16 through channel 20. In accordance with some embodiments of applicant's teachings the live animal is, for example, but not limited to, a rodent, rabbit, dog, pig, monkey, mouse, rat, or guinea pig.

To aid in connecting the device 10 to the circulatory system of a live animal or human, one or both of the opening 18 and channel 20 can feature a flexible tubing 28, 30, respectively, connecting the device 10 to the live animal or human. This allows for the device 10 to be placed remote from the live animal, but also allows for movement of the live animal without damaging the device and/or disconnecting the device from the live animal.

In accordance with some embodiments of the applicant's teachings, opening 18 and/or channel 20 can comprise, for example, but not limited to, a catheter or a cannula (not illustrated) to attach the device 10 to the live animal or human.

In accordance with some embodiments of applicant's teachings, the probe 12 is a solid phase microextraction (SPME) probe. According to the various embodiments of applicant's teachings, the SPME probe 12 comprises a fiber 32 extending into the cavity 16 of the housing 14. The fiber 32 is adapted to extract components, such as, for example, analytes, from the fluid received in the cavity 16.

The SPME fiber 32 can be extended into the cavity 16 to extract target components from the fluid, and then be retracted from the cavity 16 and device 10 for analysis. SPME probe 12 can comprise a plunger 34 adapted to extend and retract fiber 32 into the cavity 16 of the housing 14.

In accordance with various embodiments of applicant's teachings at least one of a wall 36 that defines the cavity 16 is adapted to sealingly receive therethrough at least a portion of the probe 12. In some embodiments of applicant's teachings, the wall 36 of the cavity 16 comprises, for example, but not limited to, a septum 38.

In some embodiments of applicant's teachings, the probe 12 can comprise a needle 40 adapted to pierce the septum 38.

Figure 1B:
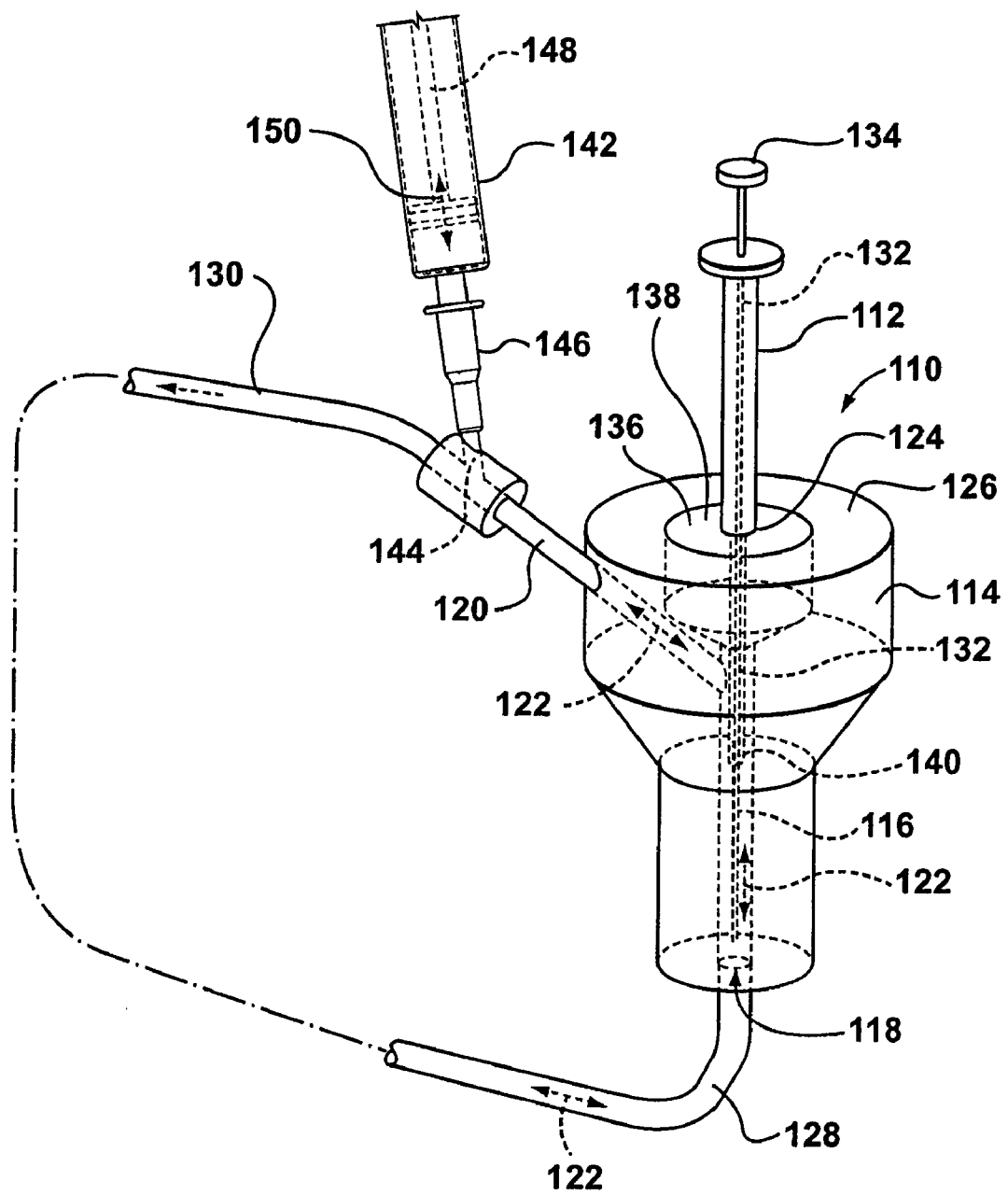
FIG. 1b is a perspective view of some alternative embodiments of the device of applicant's teachings.

Referring now to FIG. 1b, some embodiments of alternative aspects of applicant's teachings is shown. The device 110 comprises a housing 114 defining a cavity 116. The housing 114 has at least one opening 118 to allow fluid flow into and out of the cavity. For the device 110 illustrated in FIG. 1b, two openings are provided, namely, opening 118 and a channel 120 that allow fluid to flow through the cavity 116 in the direction of arrows 122. For the embodiments illustrated, the probe 112 is insertable into the cavity 116 of the housing 114 through an opening 124 in the top surface 126 of the housing 114.

In accordance with various embodiments of applicant's teachings the device 110 is a connected to a live animal or human (not illustrated). In accordance with some embodiments of applicant's teachings the live animal is, for example, but not limited to, a rodent, rabbit, dog, pig, monkey, mouse, rat, or guinea pig.

To aid in connecting the device 110 to the live animal or human, one or both of the opening 118 and channel 120 can feature a flexible tubing 128, 130, respectively, connecting the device to the live animal or human. This allows for the device 110 to be placed remote from the live animal, but also allows for movement of the live animal without damaging the device and/or disconnecting the device from the live animal.

In accordance with some embodiments of the applicant's teachings, opening 118 and/or channel 120 can comprise, for example, but not limited to, a catheter or a cannula (not illustrated) to attach the device 110 to the live animal or human.

In accordance with some embodiments of applicant's teachings, the probe 112 is a solid phase microextraction (SPME) probe. According to the various embodiments of applicant's teachings, the SPME probe 112 comprises a fiber 132 extending into the cavity 116 of the housing 114. The fiber is adapted to extract components, such as, for example, analytes, from the fluid received in the cavity 116.

The SPME fiber 132 can be extended into the cavity 116 to extract target components from the fluid, and then be retracted from the cavity 116 and device 110 for analysis. SPME probe 112 can comprise a plunger 134 adapted to extend and retract fiber 132 into the cavity 116 of the housing 114.

In accordance with various embodiments of applicant's teachings at least one of a wall 136 that defines the cavity 116 is adapted to sealingly receive therethrough at least a portion of the probe 112. In some embodiments of applicant's teachings, the wall 136 of the cavity 116 comprises, for example, but not limited to, a septum 138.

In some embodiments of applicant's teachings, the probe 112 can comprise a needle 140 adapted to pierce the septum 138.

In some embodiments of applicant's teachings of FIG. 1b, the fluid pump is, for example, but not limited to, a syringe 142. The syringe can be connected to the channel 120 through a splitter 144, such as, for example, but not limited to, a Y-adapter. Moreover, in accordance with some embodiments of applicant's teachings, a luer lock 146 can be provided to connect the syringe 142 to the channel 120.

The push/pull action on a plunger 148 of the syringe 142 (as shown by arrows 150) causes fluid to flow into and out of the cavity 116 as shown by arrows 122. In some embodiments of applicants' teachings, the fluid can be returned to the source via opening 118. In other embodiments of applicants' teachings, the splitter 144 can comprise a check valve (not illustrated) before the syringe 142 to allow the fluid to move in one direction and return to the source via channel 130.

Figure 2A:
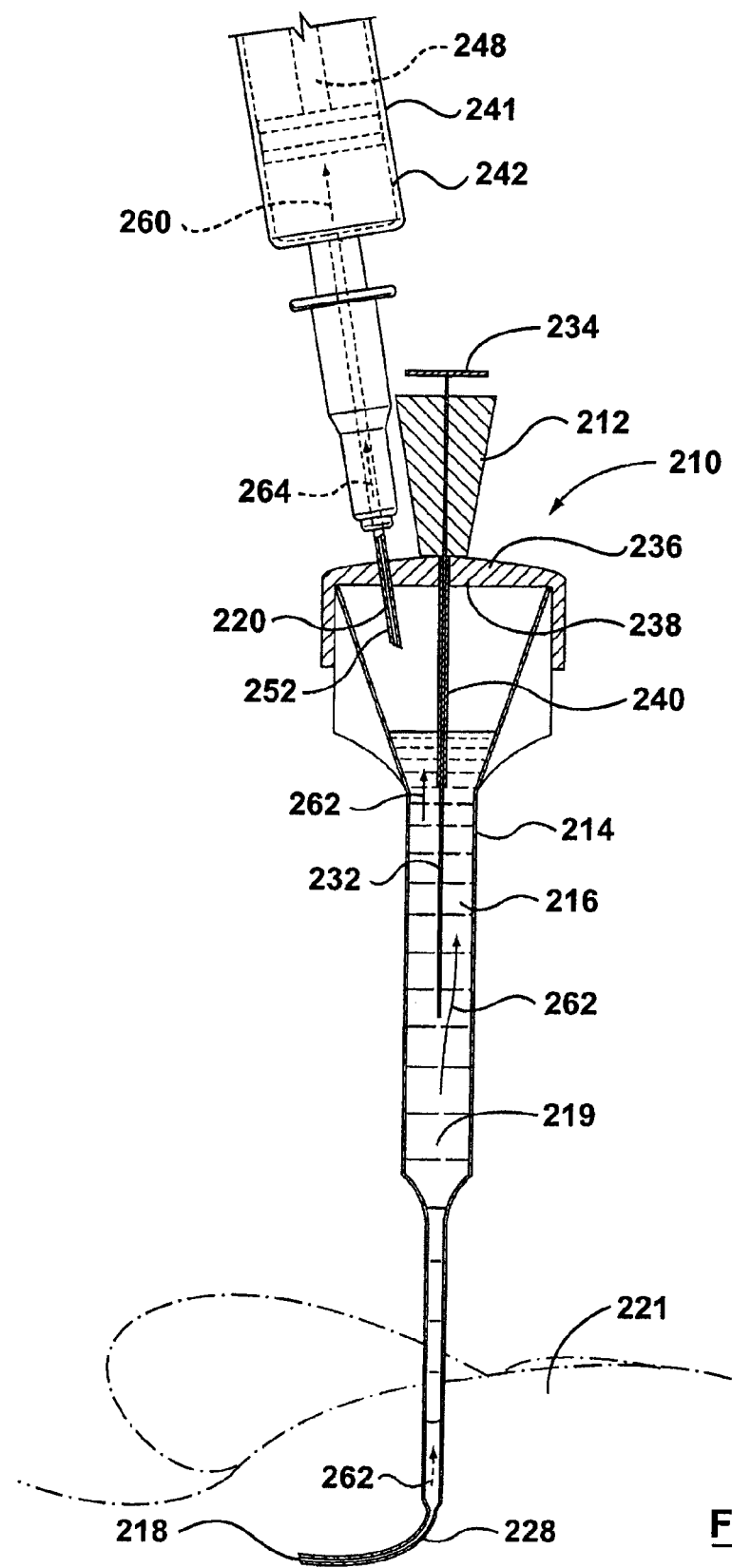
FIGS. 2a and 2b, are cross-sectional views of some further embodiments of applicant's teachings.
Figure 2B:
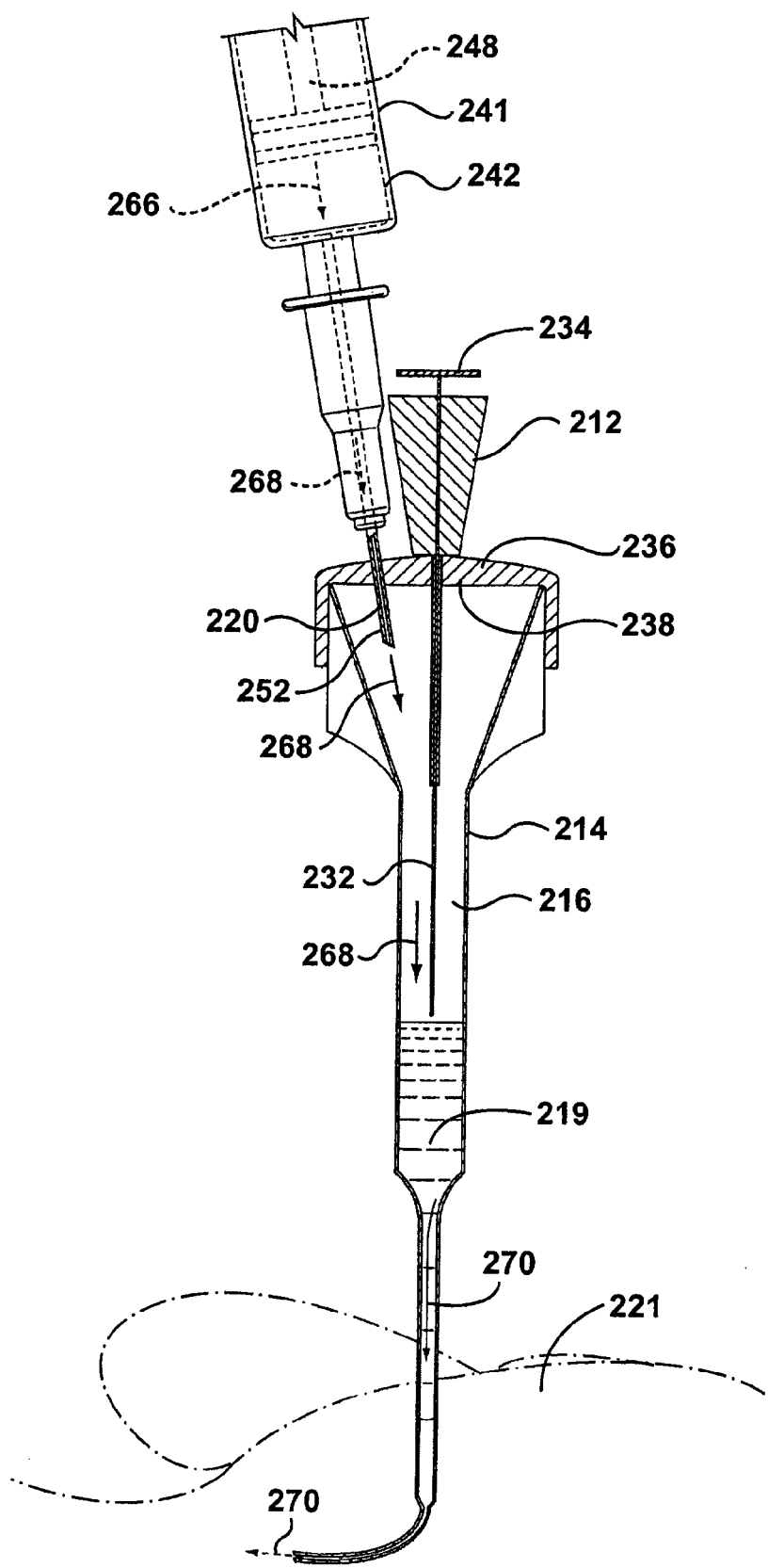

Yet further various embodiments according to applicant's teachings are shown in FIGS. 2A and 2B. Referring now to FIG. 2A, the device 210 comprises a housing 214 defining a cavity 216. The housing 214 has at least one opening 218 to allow fluid 219 to flow into and out of the cavity 216. For the device 210 illustrated in FIGS. 2A and 2B, two openings are provided, namely, opening 218 and a channel 220 that cooperate to allow fluid to flow into and out of the cavity 216, as will hereinafter be explained. For the embodiments illustrated, the probe 212 is insertable into the cavity 216 of the housing 214 through the top surface 236 of the housing 214, as will hereinafter be explained.

In accordance with various embodiments of applicant's teachings the device 210 is a connected to a live animal or human 221. In accordance with some embodiments of applicant's teachings the live animal is, for example, but not limited to, a rodent, rabbit, dog, pig, monkey, mouse, rat, or guinea pig.

To aid in connecting the device 210 to the live animal or human, the opening 218 can feature flexible tubing 228 connecting the device 210 to the live animal or human. This allows for the device 210 to be placed remote from the live animal, but also allows for movement of the live animal without damaging the device 210 and/or disconnecting the device 210 from the live animal 221.

In accordance with some embodiments of the applicant's teachings, opening 218 can comprise, for example, but not limited to, a catheter or a cannula (not illustrated) to attach the device 210 to the live animal of human.

In accordance with some embodiments of applicant's teachings, the probe 212 is a solid phase microextraction (SPME) probe. According to the various embodiments of applicant's teachings, the SPME probe 212 comprises a fiber 232 extending into the cavity 216 of the housing 214. The fiber 232 is adapted to extract components, such as, for example, analytes, from the fluid received in the cavity 216.

The SPME fiber 232 can be extended into the cavity 216 to extract target components from the fluid, and then be retracted from the cavity 216 and device 210 for analysis. SPME probe 212 can comprise a plunger 234 adapted to extend and retract fiber 232 into the cavity 216 of the housing 214.

In accordance with various embodiments of applicant's teachings at least one of a wall 236 that defines the cavity 216 is adapted to sealingly receive therethrough at least a portion of the probe 212. In some embodiments of applicant's teachings, the wall 236 of the cavity 216 comprises, for example, but not limited to, a septum 238.

In some embodiments of applicant's teachings, the probe 212 can comprise a needle 240 adapted to pierce the septum 238.

In some embodiments of applicant's teachings of FIGS. 2A and 2B, a fluid pump 241 is provided such as, for example, but not limited to, a syringe 242. For some embodiments of applicant's teachings, the syringe can be connected to the device 210 by a needle 252. The needle 252 pierces septum 238 and, for this illustrative example, forms channel 220. As shown in FIGS. 2A and 2B the needle 252 of the syringe 242, and the needle 240 of the probe 240 pierce septum 238 generally side-by-side.

It can be appreciated, however, that for some embodiments of applicant's teachings, the syringe 242 can be connected to the channel 220 through a splitter (not shown), such as, for example, but not limited to, a Y-adapter, similar to that shown for the various embodiments of applicant's teachings illustrated in FIG. 1B (see for example, but not limited to, splitter 144). Moreover, in accordance with some embodiments of applicant's teachings, syringe 242 can be connected to the channel through a luer lock (not illustrated).

The push/pull action on a plunger 248 of the syringe 242 causes fluid 219 to flow into and out of the cavity 216 as will hereinafter be explained.

In particular, having regard to FIG. 2A, pulling the plunger 248 of syringe 242 in the direction of arrow 260 draws fluid 219 from the source of fluid (typically a live animal or human) to enter opening 218 and into the cavity 216, as indicated by arrows 262. Upon entering the cavity 262, the fluid 219 contacts the fiber 232 of the SPME probe 212. The fluid 219 drawn into the cavity can be drawn up through the needle 252 and into the syringe 242, as indicated by arrows 264, however, this will not affect operation of the SPME probe 212.

After a predetermined time, the plunger 248 is pushed or depressed in the direction of arrow 266 which pushes the contents of the syringe in the direction of arrow 268 and into the cavity 216 thereby pushing the fluid 219 back into the source of the fluid (again, typically a live animal or human) through opening 218, as indicated by arrows 270.

In accordance with various embodiments of applicant's teachings, a method of extracting components contained in a fluid is will now be discussed. The method is discussed in relation to the various embodiments of applicant's teachings shown in FIGS. 1A, 1B, 2A and 2B, but is not intended to be limited to only those embodiments.

The method comprises placing a housing (for example 14, 114, or 214) defining a cavity (for example 16, 116, 216) in fluid contact with a source of fluid having components to be extracted therefrom. The source of fluids is typically a live animal or human. Examples of live animals can include, but not limited to, rodents, rabbits, dogs, pigs, monkeys, mice, rats, or guinea pigs.

Next at least a portion of a probe (for example, fiber 32, 132, 232 of SPME probe 12, 112, 212, respectively) to extract the components contained in the fluid is inserted into the cavity of the housing. For the various embodiments illustrated in FIGS. 1A, 1B, 2A and 2B, the fiber 32, 132, and 232, respectively, is inserted into the respective cavities 16, 116, 216, by depressing a plunger 34, 134, 234 of probe 12, 112, 212, respectively.

Fluid is then drawn from the source of fluid into the cavity by action of a fluid pump (for example, the circulatory system of a live animal or human in FIG. 1A, or a syringe 142, 242, as illustrated in FIGS. 1B, and 2A, 2B, respectively) so that the fluid contacts the at least a portion of the probe (for example fiber 32, 132, 232) within the cavity.

After fluid has been in contact with the fiber 32, 132, 232 of the respective probes 12, 112, 212, for a predetermined amount of time, the fluid in the cavity is returned to the source of fluid. The length of time the probe is in contact with the component to be extracted is determined by the component in the fluid to be extracted.

In accordance with some embodiments of applicant's teachings, the fluid flows into and out of the cavity through the same fluid flow path between the cavity and the source of fluid (see for example, through opening 218 for the some embodiments illustrated in FIGS. 2A and 2B). In accordance with some embodiments of applicant's teachings, a second fluid flow path is provided so that fluid is drawn from the source of fluid into the cavity through one of the fluid flow paths to contact at least a portion of the probe, and the fluid is returned to the source of fluid through the other of the fluid flow paths (see for example, openings 18, 118 and channels 20, 120, respectively, for the some embodiments illustrated in FIGS. 1A and 1B).

After the targeted components in the fluid have been extracted by the probe they can be analyzed as desired.

In vivo microextraction for pharmacokinetic studies with small animals requires the construction of special SPME probes and interfaces to the source of fluid having the components to be extracted. Solid phase microextraction, is based on fibers coated with biocompatible materials that are exposed to the sample and then removed and analyzed. This technique causes minimal disturbances to the investigated system, as no liquid and only small fractions of analytes are removed (Pawliszyn, 2003, Aust J Chem 56, 155-158; Musteata, et al., 2006, Clin Chem 52, 708-715; Pawliszyn, J. & Editor, 2002 Comprehensive Analytical Chemistry, Amsterdam: Elsevier Science BV, 37, 1131).

The most widely used technique of sampling with SPME consists of exposing a small amount of extracting phase (coating) associated with a fiber to the sample, such as a fluid having a targeted component or analytes to be extracted, for a predetermined amount of time. The diffusion of analytes from the matrix into the coating begins as soon as the coated fiber has been placed in contact with the sample. If the extraction time is long enough, concentration equilibrium is established between the sample matrix and the extraction phase. When equilibrium conditions are reached, exposing the fiber for a longer time does not result in accumulation of more analytes. Typically, the microextraction process is considered to be complete when the analyte concentration has reached distribution equilibrium between the sample matrix and the fiber coating.

When the sample volume is large, the number of moles of analyte, n, extracted by the coating can be calculated as:

$$n = K_{fs} \cdot V_f \cdot C_0 \tag{1}$$

where $C_0$ is the initial concentration of a given analyte in the sample, $V_f$ is the fiber coating volume, and $K_{fs}$ is the distribution coefficient of the analyte between the fiber coating and sample matrix (Pawliszyn, J. & Editor, 2002 Comprehensive Analytical Chemistry, Amsterdam: Elsevier Science BV, 37, 1131).

Equation 1 indicates that the amount of analyte extracted onto the coating (n) is linearly proportional to the analyte concentration in the sample ($C_0$), and points to the usefulness of the technique when the volume of the sample is unknown. In this equation, which is the basis of equilibrium calibration techniques, the amount of extracted analyte is independent of the volume of the sample. In practice, there is no need to collect a defined sample prior to analysis, as the fiber can be exposed directly to the flowing blood, ambient air, water, etc. The amount of extracted analyte will correspond directly to its concentration in the matrix, without depending on the sample volume.

The time to reach the extraction equilibrium, ranging from minutes to hours, is dependent on the agitation conditions, the physicochemical properties of analytes and the fiber coating, and the physical dimensions of the sample matrix and the fiber coating. The amount of analyte extracted onto the fiber coating is at a maximum when equilibrium is reached, thus achieving the highest sensitivity. If sensitivity is not a major concern for analysis, shortening the extraction time is desirable. For these circumstances, the extraction is stopped and the fiber is analyzed before the equilibrium is reached. The kinetics of absorption of analytes onto a fiber coating can be described as:

$$n = n_0 \cdot (1 - e^{-a \cdot t}) \tag{2}$$

where $n_0$ is the amount of analyte absorbed onto the fiber at equilibrium, t is the extraction time, and a is a time constant, representing how fast an equilibrium can be reached (Ai, 1997, Anal Chem 69, 1239-1236).

In contrast, when an SPME coating that is preloaded with a standard compound is exposed to an agitated sample matrix, desorption of the compound from the fiber occurs. The desorbed compound diffuses through the boundary layer into the bulk of sample matrix. The amount Q of standard remaining on the coating after a time t can be described as:

$$Q = q_0 \cdot e^{-a \cdot t} \tag{3}$$

where $q_0$ is the initial amount of standard present onto the fiber.

The constant a in equation 2 for absorption has the same definition as constant a in equation 3 for desorption. The value of constant a, for the same analyte, should be the same for both absorption and desorption of the analyte, under the same experimental conditions (i.e., sample bulk velocity and temperature).

Rearrangement of equations 2 and 3 leads to:

$$\frac{n}{n_0} + \frac{Q}{q_0} = 1 \tag{4}$$

Equation 4 demonstrates that the sum of $Q/q_0$ (desorption) and $n/n_0$ (absorption) should equal unity at any desorption/absorption time. This implies the isotropy of absorption and desorption of an analyte onto and from an SPME fiber. The isotropy of absorption and desorption in SPME allows for the calibration of absorption using desorption. This is especially important for the calibration of on-site, in situ, or in vivo analysis, because control of the agitation conditions of the matrix is sometimes difficult, and direct spiking of standards into the matrix is typically not possible in these cases (Chen and Pawliszy, 2004, Anal Chem 76, 5807-5815).

When application of a standard for kinetic calibration is undesirable (or a suitable standard is not available), pre-equilibrium extraction can be calibrated by two successive extractions from the same sample. In this case, the sampling time for the two extractions must be different and the sample flow rate should be constant. For calculation of the amount of analyte extracted at equilibrium, equation 2 can be applied for both extractions:

$$n_1 = n_0 \cdot (1 - e^{-a \cdot t_1}) \tag{5}$$

$$n_2 = n_0 \cdot (1 - e^{-a \cdot t_2}) \tag{6}$$

where $n_1$ and $n_2$ represent the amount of analyte extracted at times $t_1$ and $t_2$.

Rearrangement of equations 5 and 6 leads to equation 7 that can be used to determine $n_0$, the amount of analyte extracted at equilibrium:

$$(1 - n_1/n_0)^{t_2/t_1} + n_2/n_0 = 1 \tag{7}$$

In addition to convenient in vivo applications, SPME is useful for determining free concentrations (Musteata, et al., 2006, Clin Chem 52, 708-715; Musteata and Pawliszyn, 2005, J Proteome Res 4, 789-800; Musteata and Pawliszyn, 2005, J. Pharm. Biomed. Anal. 37, 1015-1024). Briefly, in the presence of an SPME fiber, the amount n (moles) of drug extracted by the fiber from the solution will be in equilibrium with the free concentration in solution. The free concentration of drug remaining in solution is then given by:

$$C_{free} = \frac{n}{f_c} \quad (8)$$

where $f_c$ is the fiber constant and represents the product of the partition coefficient of the drug (between fiber and solution) and the volume of the fiber (for liquid coatings) or the active surface of the fiber (for solid coatings). The fiber constant can be readily determined by extraction from standard solutions of the drug in PBS or "plasma water," as the drug concentration in PBS is considered to be equal to the free concentration (Musteata and Pawliszyn, 2005, J Proteome Res 4, 789-800).

For fast equilibration, the blood should be flowing through the interface. However, if sensitivity or a longer extraction time is not an issue, extraction in static conditions can be employed. In this case, the interface is first filled with blood, then the fiber is introduced for extraction, and finally the blood is returned into the body. Damage to the catheters and interface by the animals is prevented by mounting the interface on top of the cage, out of the animal's reach. Because the interface (with or without the attached syringe) is free to rotate, the danger of twisting the tubing is very low; catheter twisting can also be prevented by using a movement-responsive cage (Zhu et al., 2005, Current Separations 21, 37-44).

The sampling process does not require handling of the animal, especially when the syringe pump is used. Because the animal is less stressed, the pharmacokinetic data is more relevant, and fewer animals are required to obtain reproducible data.

Applicant's teachings, for example, but not limited to, allow for fast in vivo microextraction for PK studies in rats and mice.

Aspects of the applicant's teachings may be further understood in light of the following examples, which should not be construed as limiting the scope of the present teachings in any way.

EXAMPLES

Preparation of SPME Probes: Biocompatible SPME fibers are prepared by anodic oxidation of the pyrrole monomer (from Sigma/Aldrich, Mississauga, ON; Musteata, et al., 2006, Clin Chem 52, 708-715).

Preparation of SPME Devices: The device for in vivo extraction consists of a flexible thin wire coated with biocompatible extraction phase and housed inside a hypodermic tubing (medical grade stainless steel, Type 316 S/S-23 gauge, from Small Parts Inc., Miami Lakes, Fla.). The assembly is sealed with a piece of PDMS green septum (from Supelco, Bellefonte, Pa.).

Interfaces for in Vivo Application of SPME: For studies in rats, the interface consists of a Y-adapter (see FIG. 1B). The Y-adaptor can be manufactured from, for example, but not limited to, Teflon®, stainless steel and polyurethane.

Standard Compounds and Probe Characterization: Diazepam, nordiazepam, oxazepam, diazepam-D5, and carbamazepine standards (1 mg/mL in methanol) can be obtained from Cerilliant (Austin, Tex.). The standards are diluted in methanol or phosphate-buffered saline, pH 7.4 (PBS), to prepare mixtures of various concentrations for use in sample preparation and instrument calibration. HPLC grade acetonitrile and methanol can be obtained from Fisher Scientific (Fair Lawn, N.J.). Fresh rat whole blood (sterile, with EDTA as anticoagulant) can be obtained from Bioreclamation (Hicksville, N.Y.). Deionized water can be obtained from a Barnstead/Thermodyne NANO-pure water system (Dubuque, Iowa). The drugs investigated are considered to be stable in whole blood over the course of the calibration procedure (less than 10 minutes at 38° C.).

All of the probes used in the study are desorbed in parallel in plastic inserts with 20 μL desorption solvent consisting of acetonitrile and water (75:25) with 0.1% acetic acid. Lorazepam is included in the desorption solution as an internal standard (25 ng/mL), to control for variation in injection volume. The probes are removed after one minute, when desorption is complete. The resultant solution is injected automatically in an LC-MS/MS (liquid chromatography coupled to tandem mass spectrometry) system.

LC-MS/MS Assay: Analyses is performed on an LC-MS/MS system consisting of a Shimadzu (Kyoto, Japan) 10AVP LC with a system controller and dual binary pumps interfaced to a CTC-PAL autosampler and an MDS Sciex API 3000 tandem mass spectrometer with a Turbo Ion Spray source (Toronto, ON). Chromatographic separations are carried out on a Waters Symmetry Shield RP18, 50×2.1 mm id packed with 5 μm particles (Millford, Mass.), guarded by an on-line filter (0.5 μm). The mobile phase consisted of: (A) acetonitrile/water (10:90) with 0.1% acetic acid and (B) acetonitrile/water (90:10) with 0.1% acetic acid. Mobile phase flow rate was 0.5 mL/min, and the gradient used is 10% B for the first 0.5 min, ramped to 90% B over 2.0 min, held for 1.5 min, and finally returned to 10% B for 1 min. For experiments using whole blood, the mobile phase is directed to waste for the first minute of run time, to prevent electrolytes and hydrophilic proteins from entering the ion source. During this first minute, a supplementary pump is used to deliver a makeup flow to the mass spectrometer.

All components are analyzed by electrospray ionization in positive ion mode with multiple reaction monitoring. The nebulizer flow ($N_2$) is set to "8", the curtain gas ($N_2$) is "12," collision activated dissociation ($N_2$) is "12," ion spray voltage is 4500 V, and the temperature is 250° C. The following transitions are monitored: diazepam, m/z 285.2/154.1; nordiazepam, m/z 271.1/140.0; oxazepam, m/z 287.1/241.1; diazepam-D5, m/z 290.4/198.4; lorazepam, m/z 321.1/275.1. The dwell time is 200 ms for each pair, with a focusing potential of 200 V, an entrance potential of 10 V, and a collision cell exit potential of 12 V. Optimal mass spectrometer conditions are determined for all compounds by infusion of a 100 ng/mL solution in methanol:water 1:1 pumped at 1 mL/h, followed by ramping of mass spectrometer parameters. Data is collected and analyzed using the Analyst 1.4.1 software from MDS Sciex.

Animal Experiments: Male Sprague-Dawley rats (Charles River Labs, St. Constant, PQ) with an average weight of 300 g are acclimatized to their new environment for a minimum of 5 days prior to surgery. One day prior to dosing, rats are implanted with jugular vein and carotid artery catheters while under anesthesia with isoflurane (1.5% in oxygen delivered at a rate of 1 L/min). The catheters are plugged with removable metal plugs at the free end and then exteriorized by threading them under the skin and through a small incision at the nape of the neck. Animals are allowed to recover overnight prior to dosing. All rats were conscious and freely moving throughout the study. In vivo mouse experiments are conducted with conscious male Swiss Webster mice implanted with a carotid artery catheter. All procedures followed have been reviewed by the NoAb BioDiscoveries Inc. animal care committee and were performed in accordance with the principles of the Canadian Council on Animal Care (CCAC).

A device to extract components is attached to the carotid artery catheter prior to dosing each rat or mouse. To insert the probes, the tip of the SPME probe needle is used to pierce the septum of the device. The length of the fiber or wire of the probe is chosen so that the coated wire is completely exposed to the blood flow when the plunger is fully depressed. Before use, the SPME probe is sterilized in an autoclave at 121° C. and 15 psi for about 30 minutes. For validation purposes, blood draws are taken from the same interface after each sampling with SPME. All the probes are for single use.

Prior to dosing with diazepam, one blood draw (0.2 mL) is obtained from the device and simultaneously a zero time probe analysis is performed. Rats are administered diazepam by bolus i.v. injection into the jugular vein catheter. Diazepam (5 mg/mL injectable solution) is dosed at 0.5 mg/kg for equilibrium extraction and at 1 mg/kg for kinetic calibration. Diazepam-D5 is used as the standard on the fiber for kinetic calibrations. Drug concentrations are monitored for about six (6) hours after dosing with diazepam. For each time point (5, 15, 30, 45, 60, 75, 120, 180, 240 and 360 min), the probes are in place for about two (2) minutes before the stated analysis time and blood draws are performed immediately after removing the probes. After the two (2) minute extraction time, the probes are removed, rinsed with water, and stored at −20° C. until the next day, when analysis is performed. All the compounds are known to be stable on the fibers for at least 24 hours. For SPME calibration, rat whole blood is spiked with appropriate amounts of benzodiazepines and incubated with 10% $CO_2$ atmosphere. The analytical range is 3-750 ng/mL.

Conventional Plasma Sampling and Analysis: In addition to SPME sampling, 0.2 mL of blood is withdrawn from the interface at each time point. Plasma is isolated by centrifugation at 2500 rpm for 10 minutes and frozen at −20° C. in 2 mL cryovials (Wheaton Science Products, Millville, N.J.) until analysis. For analysis, 0.05 mL of plasma is mixed with 0.25 mL acetonitrile containing 25 ng/mL lorazepam as internal standard in conical centrifuge vials. After vortex mixing (2400 rpm, 5 minutes) and centrifugation (14000 rpm, 7 minutes), 0.2 mL of the supernatant is transferred to a 96-well plate and evaporated to dryness under flowing nitrogen. The residue is dissolved in 0.1 mL acetonitrile/water (75:25) on a shaking bed (150 rpm). Twenty μL is injected for analysis using the same chromatographic conditions as for the analysis of SPME probes. The linear range is 0.1-1000 ng/mL.

Data Analysis: For diazepam, the mean concentration versus time data is analyzed by a 2-compartment model ($Y=A*e^{-\alpha t}+B*e^{-\beta t}$) using WinNonlin Pro (Pharsight Corp., Mountainview, Calif.). Areas under the plasma concentration versus time curves (AUCs) represent the areas under the curve from the time of dosing and extrapolated to infinity. The distribution (α) and elimination (β) half-lives ($t_{1/2}$) are calculated as $\ln(2)/\alpha$ and $\ln(2)/\beta$, respectively. The total body clearance (CL) is estimated as: Dose/AUC. Mean residence times (MRT) are calculated as: AUMC/AUC, where AUMC denotes the area under the first moment curve. The steady-state volume of distribution ($V_{ss}$) is calculated as: CL*MRT.

For the two diazepam metabolites, nordiazepam and oxazepam, which are measured using equilibrium calibration for SPME, the mean concentration versus time data are analyzed by noncompartmental methods also using WinNonlin Pro. AUCs are calculated by the linear/log-linear trapezoidal rule. AUCs represent the areas under the curve from the time of dosing: (1) to the time ($t_{last}$) of the last measurable concentration, $C_{last}$ ($AUC_{0-tlast}$) and, (2) extrapolated to infinity ($AUC_{0-inf}$). $AUC_{0-inf}$ is estimated by the addition of $AUC_{0-tlast}$ and $C_{last}/k$, where k (or $\lambda_z$) represents the terminal elimination rate constant. K is estimated by weighted ($1/Y^2$) regression analysis of at least 4 time points from the terminal (log-linear) portion of the concentration versus time curve. Terminal elimination half-lives ($t_{1/2}$) were calculated as $\ln(2)/k$. AUMCs are also estimated from the time of dosing to the last measurable concentration ($AUMC_{0-tlast}$) and extrapolated to infinity ($AUMC_{0-inf}$) and are used to calculate the corresponding MRTs The time ($t_{max}$) at which maximum nordiazepam or oxazepam concentrations ($C_{max}$) are observed are determined from nominal values.

The in vivo microextraction methodology is evaluated through studies of diazepam pharmacokinetics in rats and carbamazepine pharmacokinetics in mice. Quantification of extracted compounds (diazepam, nordiazepam, oxazepam and carbamazepine) is performed by a highly specific and sensitive liquid chromatography tandem mass spectrometric method. In this microextraction and kinetic calibration for in vivo analysis in rats and mice, sampling devices based on hypodermic tubes with SPME fibers are developed and used for investigation of free and total concentration of diazepam and metabolites in whole blood.

Figure 3:
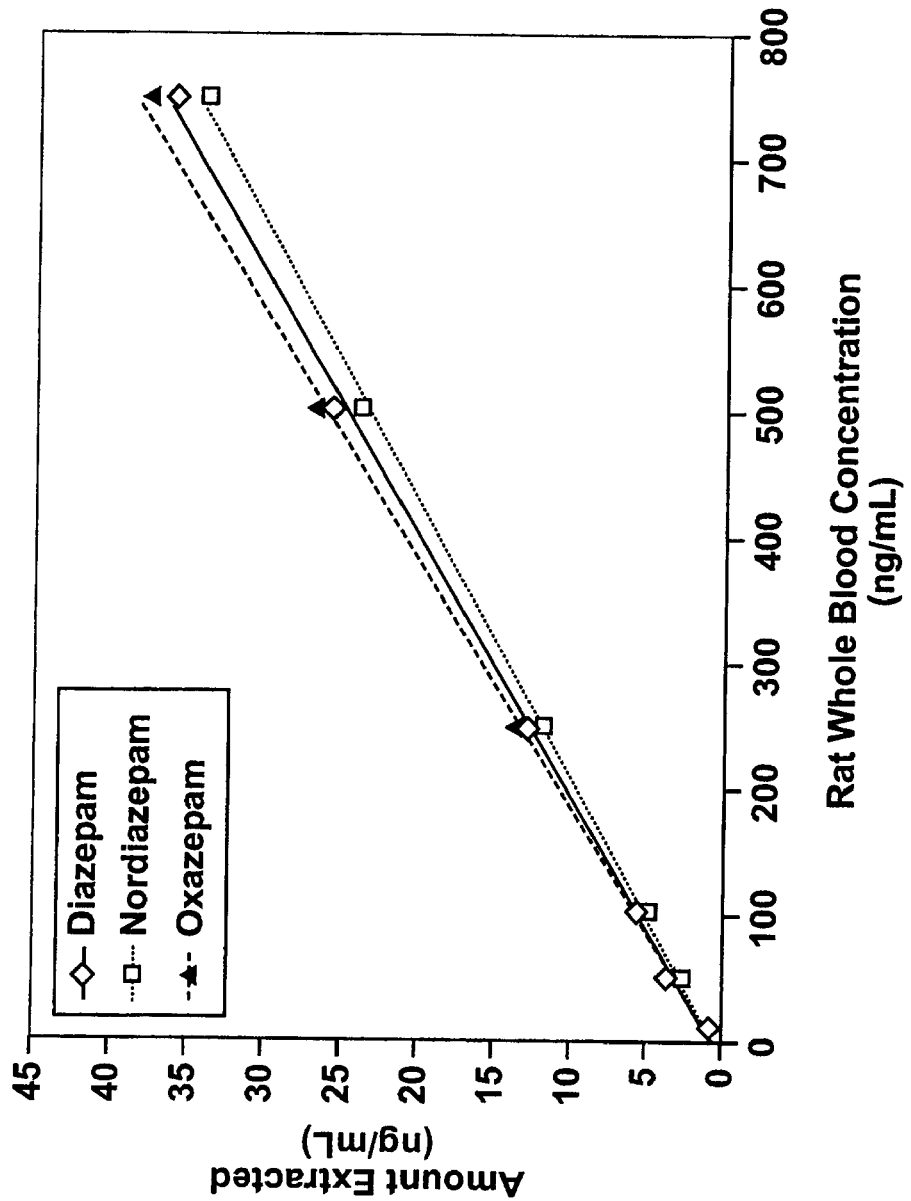
FIG. 3 is a graph of amount analyte extracted versus rat whole blood concentration.
Figure 8:
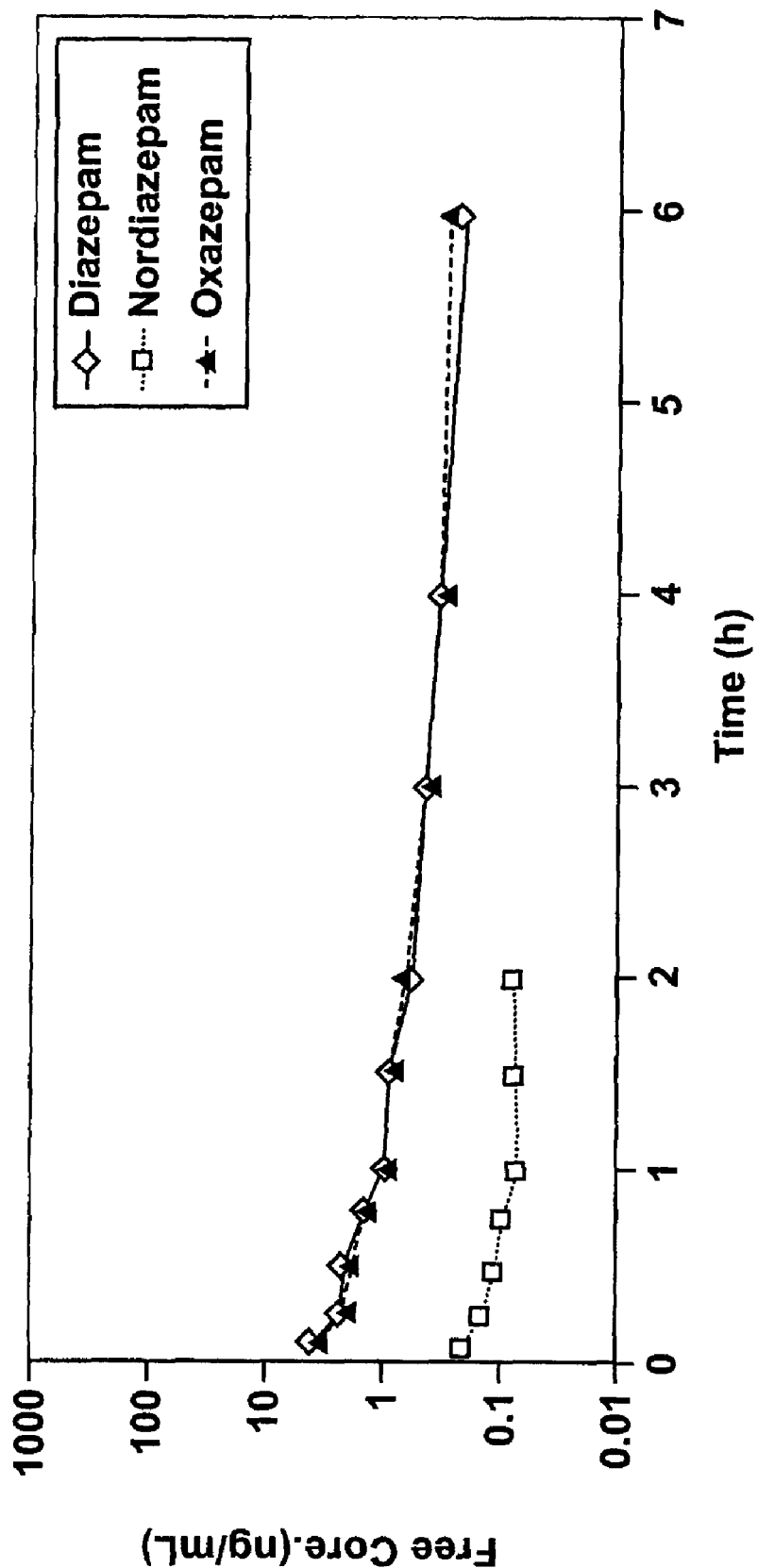
FIG. 8 is a graph of free concentrations of analytes versus time.

For quantitative analysis, calibration is performed by both equilibrium extraction and kinetic calibration. For kinetic calibration, two methods are used: standard on the fiber and double extraction. Two of the major metabolites of diazepam, nordiazepam and oxazepam, are monitored as well. In order to relate the amount of analyte extracted to its total blood concentration, calibration curves in whole blood are prepared (see FIG. 3). While the results for total concentration are more accurate when the blood used for calibration has the same binding properties as in vivo blood, reliable measurements of the free concentration can be obtained even when the concentration of plasma proteins changes during the study, because the amount of analyte extracted by SPME is inherently related to the free concentration. FIG. 8 presents the free concentration profile of diazepam, oxazepam and nordiazepam in rat whole blood.

The SPME probes are exposed to the blood flowing through the cavity of the device to extract components according to applicant's teachings. The probes are placed in the device since, unlike experiments with larger animals, it is not possible to directly insert the probes into a blood vessel of a rat or a mouse without significantly occluding it. Studies are conducted on three rats or mice in parallel.

For small animals, such as rats or mice, to maintain sufficient pressure for keeping the blood flowing through the device for extended periods of time and to prevent clotting, a syringe is used as a fluid pump to draw and push blood through the device.

Example 1

In vivo experiments are conducted with conscious male Sprague-Dawley rats implanted with jugular vein and carotid artery catheters. The catheters are plugged and exteriorized at the nape of the neck. Prior to dosing, the opening of the device is connected to the carotid artery catheter. The channel of the device is either connected to the jugular vein catheter or is connected to a syringe pump. Connecting the device to the jugular vein catheter allowed for automatic return of the arterial blood, using the pumping action of the heart of the animal. Connecting the device to a syringe allows for precise control of the blood flow rate through the device. The device and the associated tubing are kept warm at 38° C.

Rats are administered either 1 or 0.5 mg/kg diazepam by bolus injection into the jugular vein catheter. At each sampling time point, a sterile SPME device is placed through the septum into the interface so that only the coated portion of the fiber is exposed to the flowing blood. Blood flow through the device is either allowed to run freely via recirculation to the jugular vein or is induced by the push/pull action of a syringe attached to the channel.

When a syringe is used, as in for example, but not limited to FIG. 1B, 0.2 mL of blood is withdrawn at a flow rate of 0.6 mL/min and then pushed back at the same flow rate. This flow rate is well below the normal flow rate in the rat carotid artery, and induced minimal disturbance. Three push/pull cycles (20 s push followed by 20 s pull) are completed over a two minute interval of equilibrium SPME sampling. For kinetic calibration with the standard preloaded on the fiber, one push/pull cycle is performed (for about 40 seconds). For kinetic calibration by double extraction, a short cycle (about 20 seconds) is followed by a regular cycle (about 40 seconds).

The sensitivity, reproducibility and linear range of the assay are investigated by in vitro analysis of phosphate buffered saline (PBS) spiked solutions (for determination of free concentrations) and whole rat blood spiked with a series of drug concentrations. All in vitro samples are incubated at 38° C. in 10% $CO_2$ atmosphere, in order to create experimental conditions similar to in vivo sampling and to generate accurate calibrations. The linear range for diazepam, nordiazepam, and oxazepam in rat whole blood is from 3 to 800 ng/mL total concentration (FIG. 3), corresponding to about 0.18-48 ng/mL free concentration.

For validation of the in vivo sampling method taught by the applicant's teachings, blood is sampled after each probe extraction, and plasma is isolated by centrifugation. The short exposure time of the SPME devices allows for the possibility to easily perform three experiments in parallel. Also, it is possible to draw the blood through the same device that is used for the probes, resulting in less stress for the experimental animals.

Figure 4:
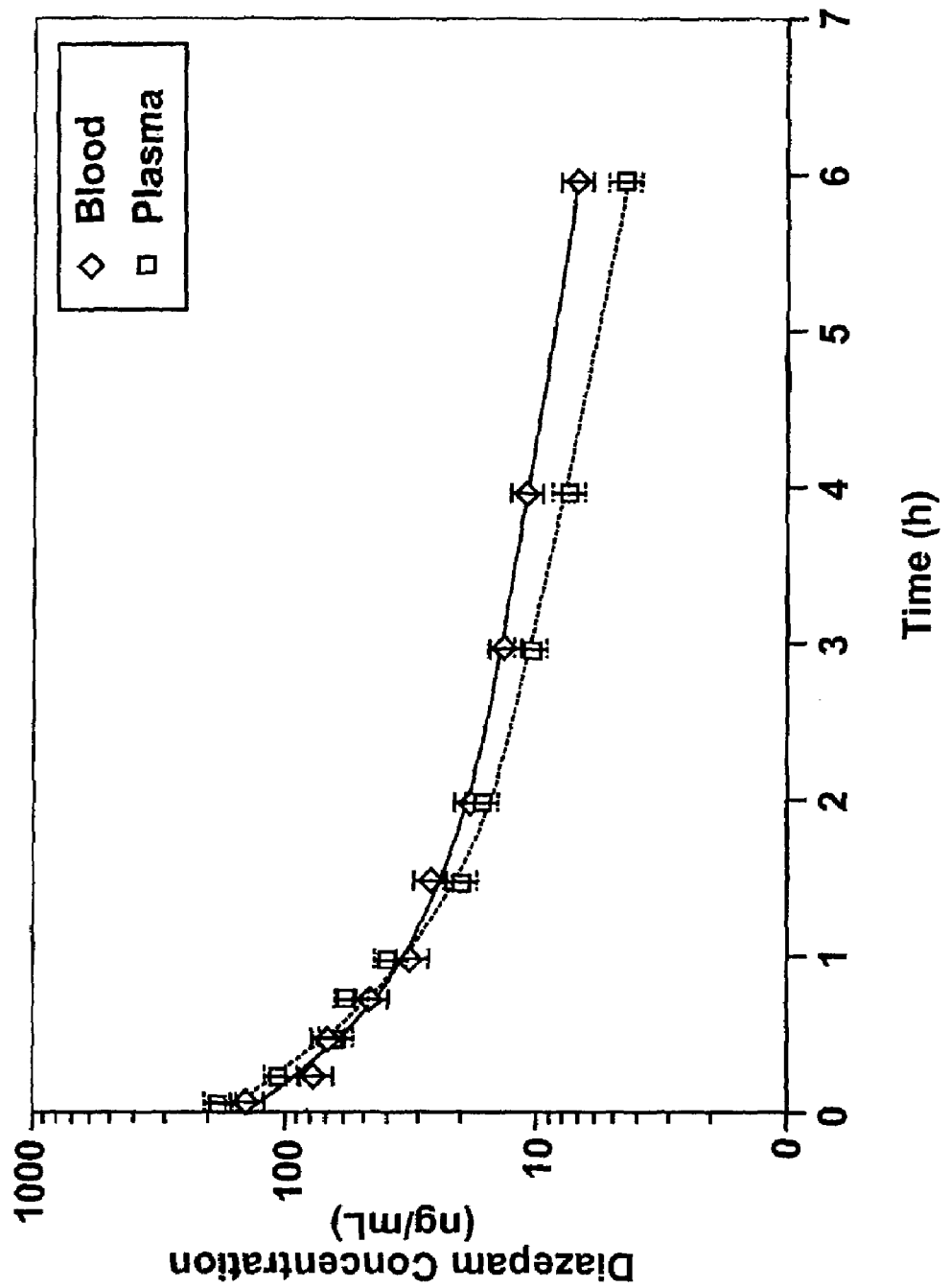
FIGS. 4 and 5 are graphs of diazepam concentration versus time.
Figure 6:
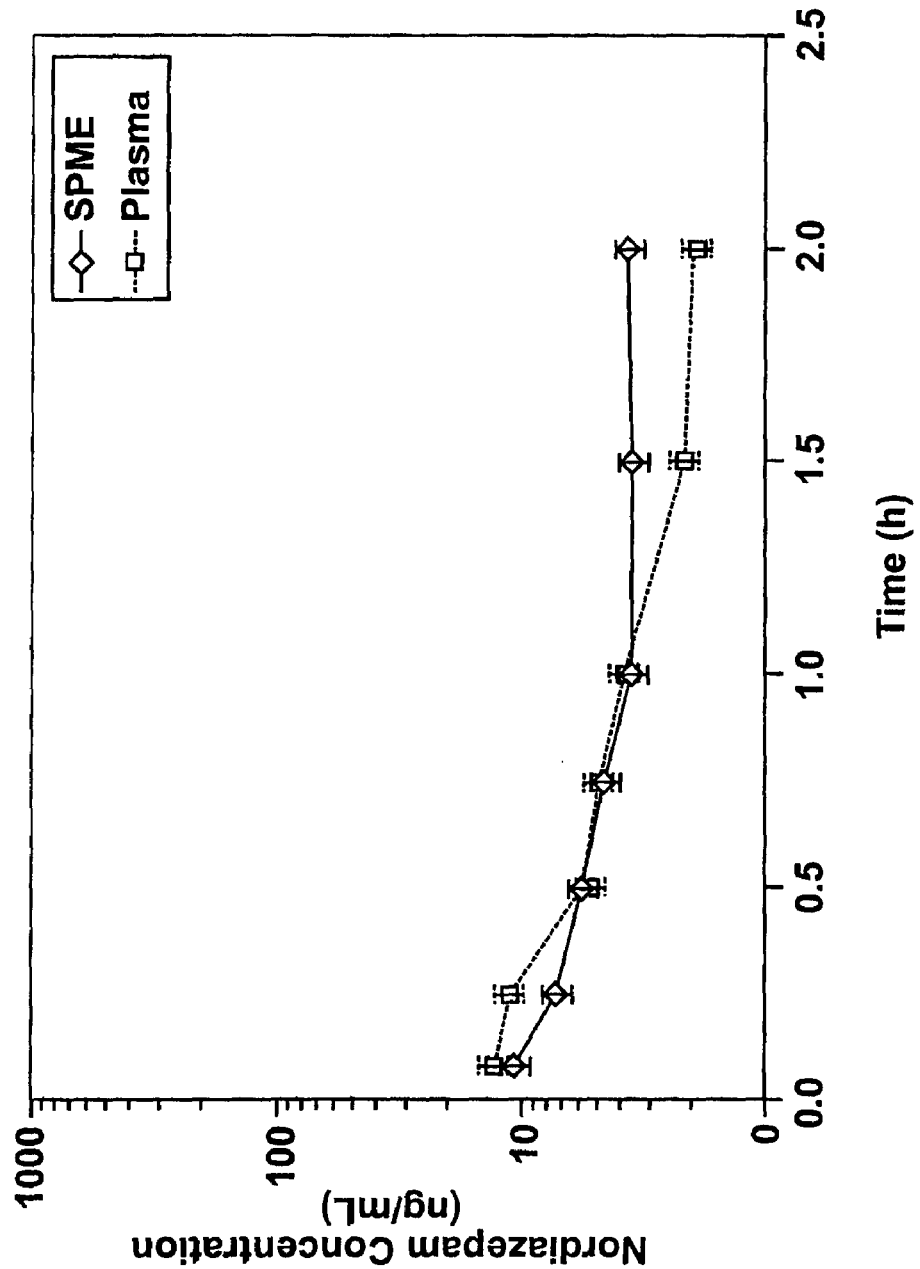
FIG. 6 is a graph of nordiazepam concentration versus time.
Figure 7:
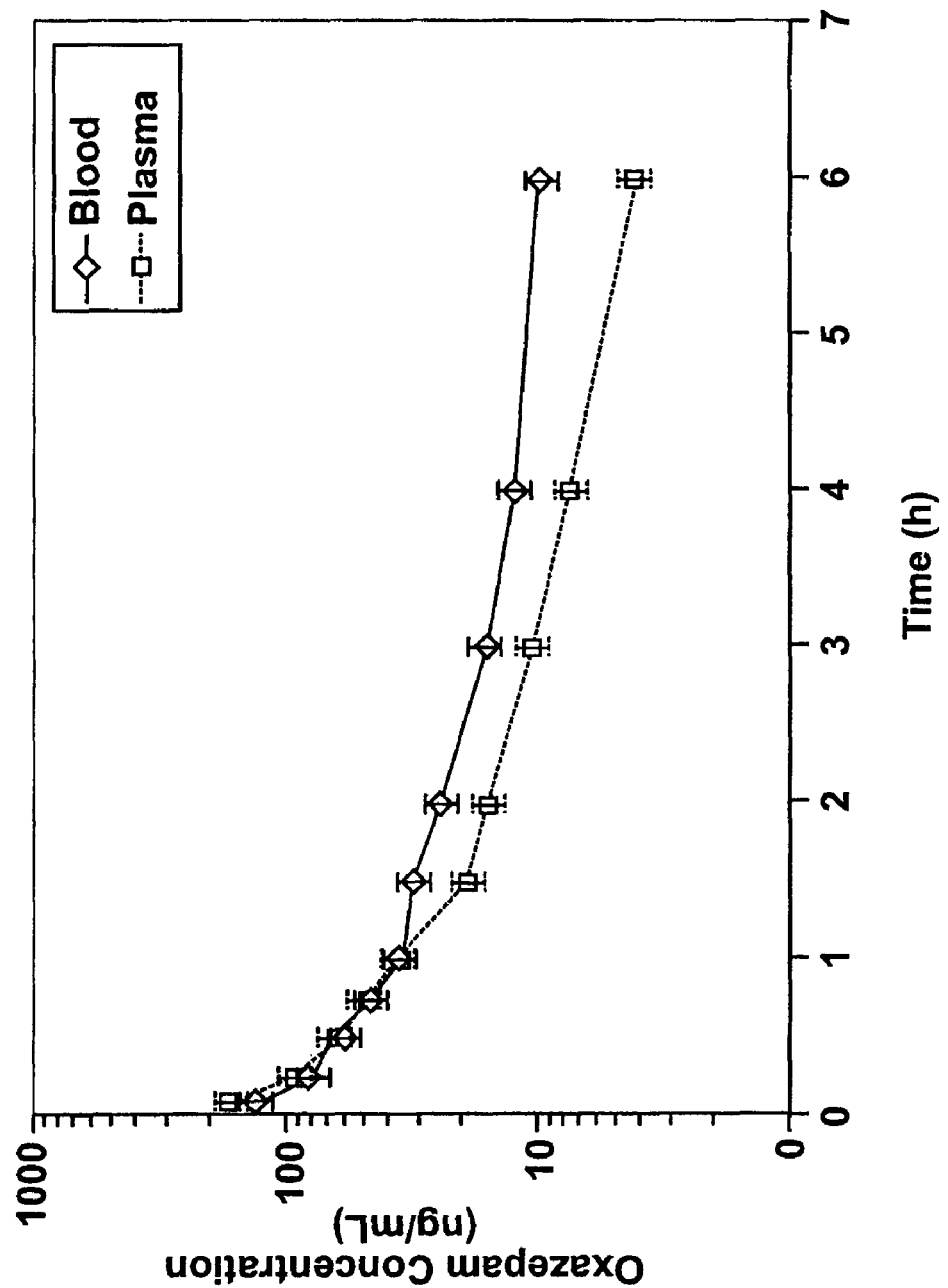
FIG. 7 is a graph of oxazepam concentration versus time.

The concentration versus time profiles for diazepam, nordiazepam, and oxazepam obtained with the probes, which measure concentrations in whole blood, are compared to the results of conventional sampling and analyses in plasma (see FIGS. 4, 6 and 7, respectively). The total amount of time required to prepare a single sample ready for LC-MS/MS analysis is up to 3 minutes in the case of SPME and 90 minutes for conventional plasma analysis.

Figure 5:
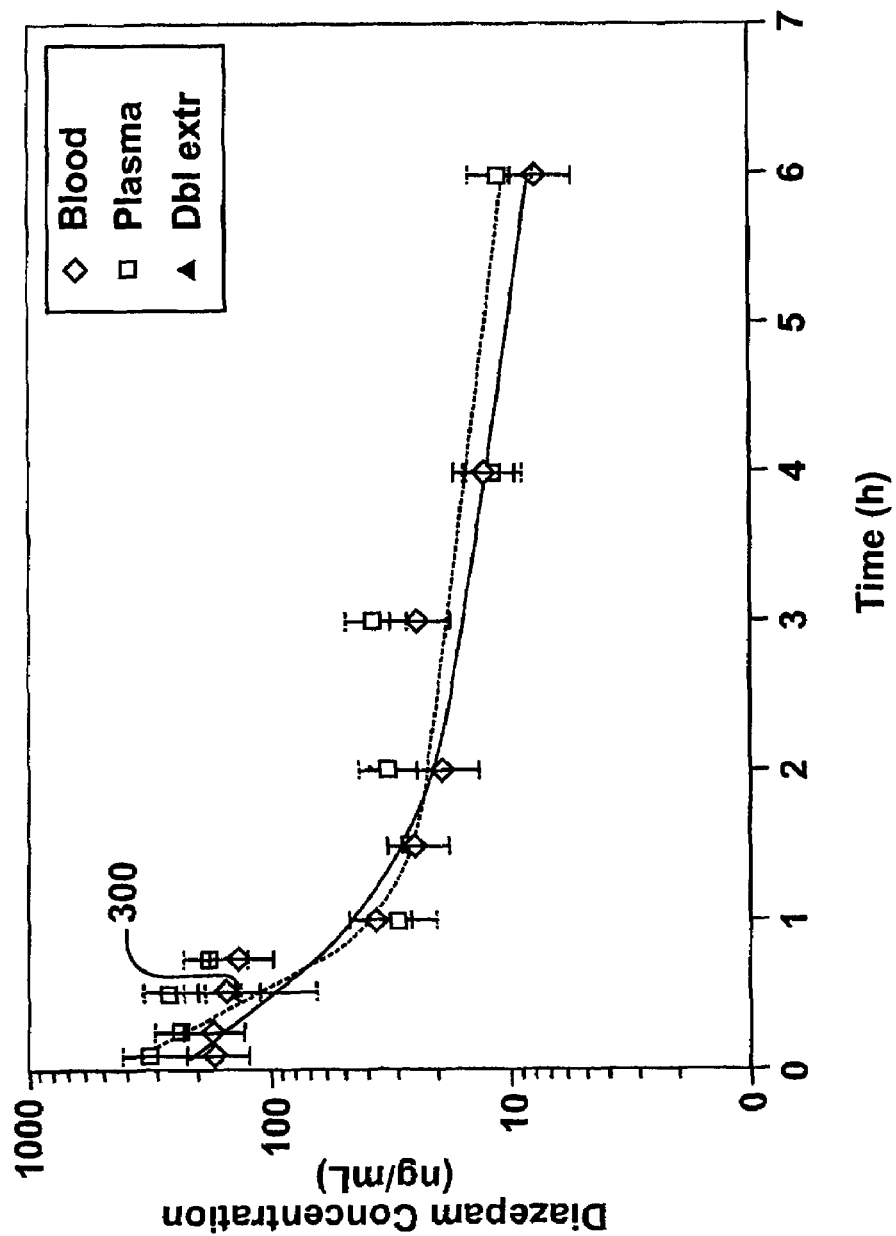

Due to the distribution of drugs into blood cells, the ratio between plasma and whole blood concentration can be anywhere from 1.35 to 2.22 (Jones and Larsson, 2004, *Ther Drug Monit* 26, 380-385). Since the distribution of diazepam in red blood cells relative to plasma is not known, no correction factor is used for the comparative graphs. Despite this, all three compounds show a good correlation between the concentration values obtained with SPME and conventional sampling followed by plasma analysis, as shown in FIGS. 4, 6 and 7. The pharmacokinetic parameters determined for diazepam are also similar between methods (see Table 1). The estimated values for clearance (CL), volume of distribution ($V_{ss}$), and the distribution and elimination half-lives ($t_{1/2}(\alpha)$ and $t_{1/2}(\beta)$, respectively determined by the SPME method with equilibrium calibration, are very similar to those estimated by conventional plasma sampling analysis. These parameters are also very similar when kinetic calibration is performed for SPME, despite the fact that greater overall variability is observed in both the blood (SPME) and plasma concentration versus time profiles (FIG. 5).

Mean blood and plasma concentrations of two of the metabolites of diazepam, nordiazepam and oxazepam, as determined by SPME (equilibrium calibration) and conventional plasma sampling and analysis, respectively, are also similar (FIG. 6 and FIG. 7). Blood concentrations of the metabolites determined in the apparent elimination phase by SPME appeared slightly higher than those determined in plasma, and therefore, the apparent elimination half-life and MRT determined by SPME are higher than those determined by conventional plasma analysis (Table 2).

All concentration versus time profiles (FIGS. 4, 6 and 7) are in good agreement with literature values (Gueorguieva et al. 2004, *J Pharmacokinet Pharmacodyn* 31, 185-213).

Kinetic calibration by double extraction is performed only for the data points collected at 30 minutes (e.g. FIG. 5, double extraction 300), as this is the first in vivo application, whereas equilibrium extraction and the standard on the fiber approach are applied for all data points.

TABLE 1

Estimated pharmacokinetic parameters determined by 2-compartment analysis of the mean diazepam concentration versus time curves following equilibrium and kinetic calibration methods.

| | | Equilibrium Calibration | | Kinetic Calibration | |
|---|---|---|---|---|---|
| Parameter | Units | Plasma | SPME/Blood | Plasma | SPME/Blood |
| Dose | mg/kg | 0.5 | 0.5 | 1 | 1 |
| AUC | h*ng/mL | 157 | 172 | 303 | 236 |
| $t_{1/2}(\alpha)$ | H | 0.301 | 0.310 | 0.198 | 0.304 |
| $t_{1/2}(\beta)$ | H | 2.26 | 2.89 | 3.84 | 3.47 |
| CL | mL/h/kg | 3193 | 2909 | 3304 | 4233 |
| AUMC | h$^2$*ng/mL | 319 | 527 | 1000 | 741 |
| MRT | H | 2.04 | 3.06 | 3.31 | 3.14 |
| $V_{ss}$ | mL/kg | 6500 | 8917 | 10921 | 13294 |

TABLE 2

Estimated pharmacokinetic parameters for the metabolites, nordiazepam and oxazepam, following i.v. bolus administration of 0.5 mg/kg diazepam.

| | | Nordiazepam | | Oxazepam | |
|---|---|---|---|---|---|
| Parameter | Units | SPME | Plasma | SPME | Plasma |
| Terminal half-life | h | 1.74 | 1.03 | 3.52 | 2.17 |
| $T_{max}$ | h | 0.0833 | 0.0833 | 0.0833 | 0.0833 |
| $C_{max}$ | ng/mL | 10.6 ± 2.64 | 12.9 ± 3.23 | 129 ± 32.3 | 165 ± 41.3 |
| $AUC_{0-tlast}$ | h*ng/mL | 9.30 | 9.34 | 149 | 124 |
| $AUC_{0-inf}$ | h*ng/mL | 18.6 | 12.2 | 199 | 137 |
| $AUMC_{0-tlast}$ | h$^2$*ng/mL | 7.86 | 6.38 | 278 | 176 |
| $AUMC_{0-inf}$ | h$^2$*ng/mL | 50.0 | 16.5 | 834 | 293 |
| $MRT_{0-tlast}$ | h | 0.845 | 0.683 | 1.86 | 1.42 |
| $MRT_{0-inf}$ | h | 2.68 | 1.35 | 4.18 | 2.14 |

Example 2

In vivo mouse experiments are conducted with conscious male Swiss Webster mice implanted with a carotid artery catheter. The catheter is plugged and exteriorized at the nape of the neck and the animal is allowed to recover. Prior to dosing, the device for component extraction, as in for example but not limited to FIGS. 2A and 2B, is connected to the carotid artery catheter and rested on the back of the animal. Mice are administered 4 mg/kg carbamazepine by bolus injection into the tail vein. One minute prior to each sampling time point, a sterile SPME device is placed through the septum into the device so that only the coated portion of the fiber is exposed to the blood. A Tubercullin® syringe is also placed through the septum of the interface parallel to the SPME device (for example, see FIGS. 2A and 2B). Blood flow through the interface is induced by the push/pull action of the syringe. Blood (50-100 μL) is withdrawn over 20 seconds and then pushed back over 20 seconds. This flow rate (0.15 to 0.3 mL/min) produces minimal disturbance to the animal. Three push/pull cycles are completed during a two-minute interval of equilibrium SPME sampling.

Figure 9:
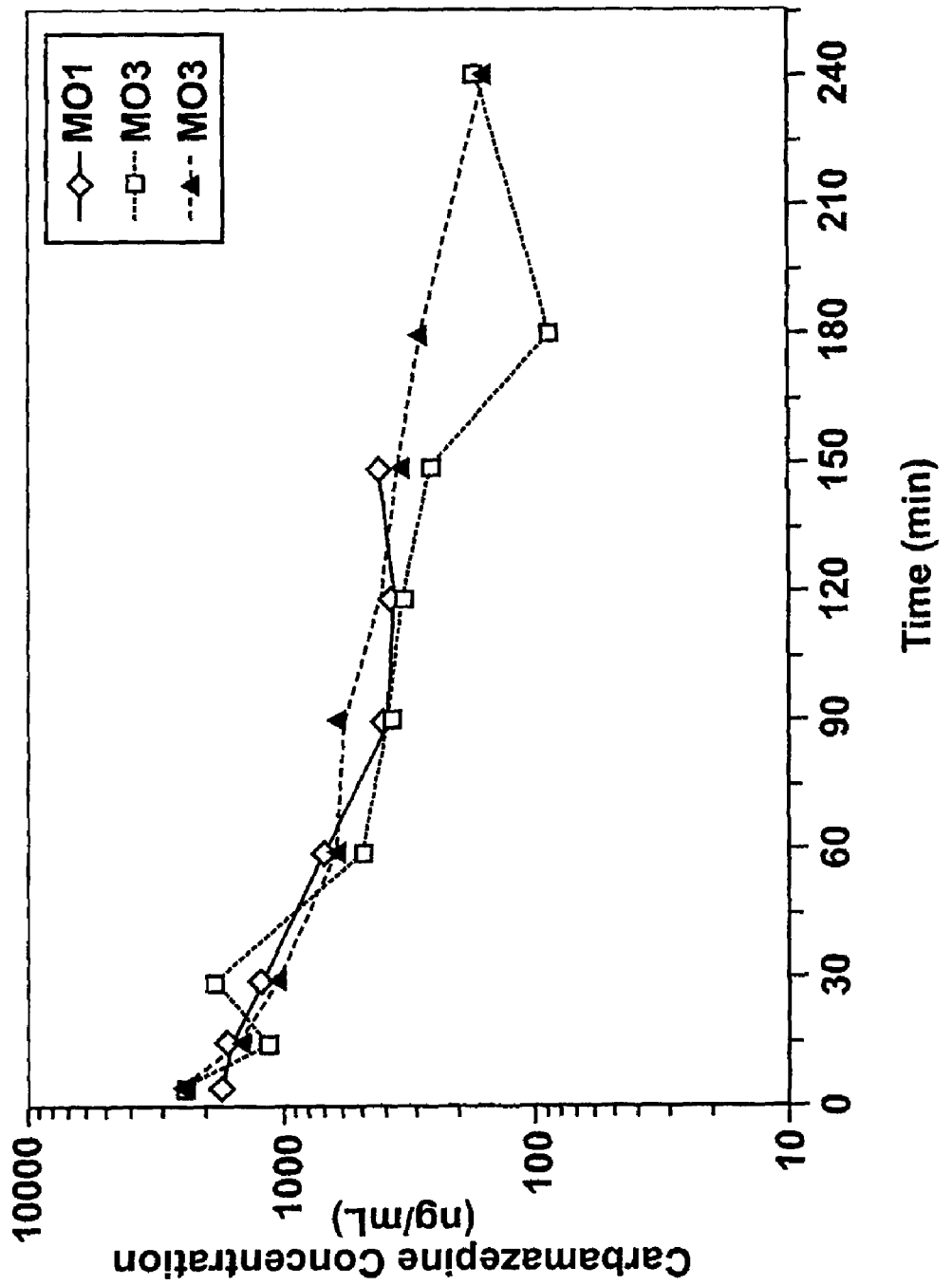
FIG. 9 is a graph of carbamazepine concentration versus time.

Desorption of the analyte from the SPME sample probes is performed in organic solvent over 30 min and then analyzed by LC-MS/MS. The whole blood concentration versus time profile of carbamazepine in the 3 mice is depicted in FIG. 9.

The sensitivity, reproducibility and linear range of the assay for quantification of carbamazepine are investigated by in vitro analysis of phosphate buffered saline (PBS) spiked solutions (for determination of free concentrations) and whole mouse blood spiked with a series of drug concentrations. All in vitro samples are incubated at 38° C. in 10% $CO_2$ atmosphere, in order to create experimental conditions similar to in vivo sampling and to generate accurate calibrations. The linear range for carbamazepine in mouse whole blood and PBS is from 1 to 500 ng/mL concentrations.

For validation of the in vivo sampling approach, the results from serial SPME sampling in 3 mice are compared to the plasma concentration versus time profile following i.v. administration of 2 mg/kg carbamazepine to a group of 21 mice. The mice are dosed with carbamazepine via the tail vein and blood is collected from 3 mice at each time point by terminal cardiac puncture. Plasma is isolated by centrifugation. Plasma samples are extracted by protein precipitation and then analyzed by LC-MS/MS.

Figure 10:
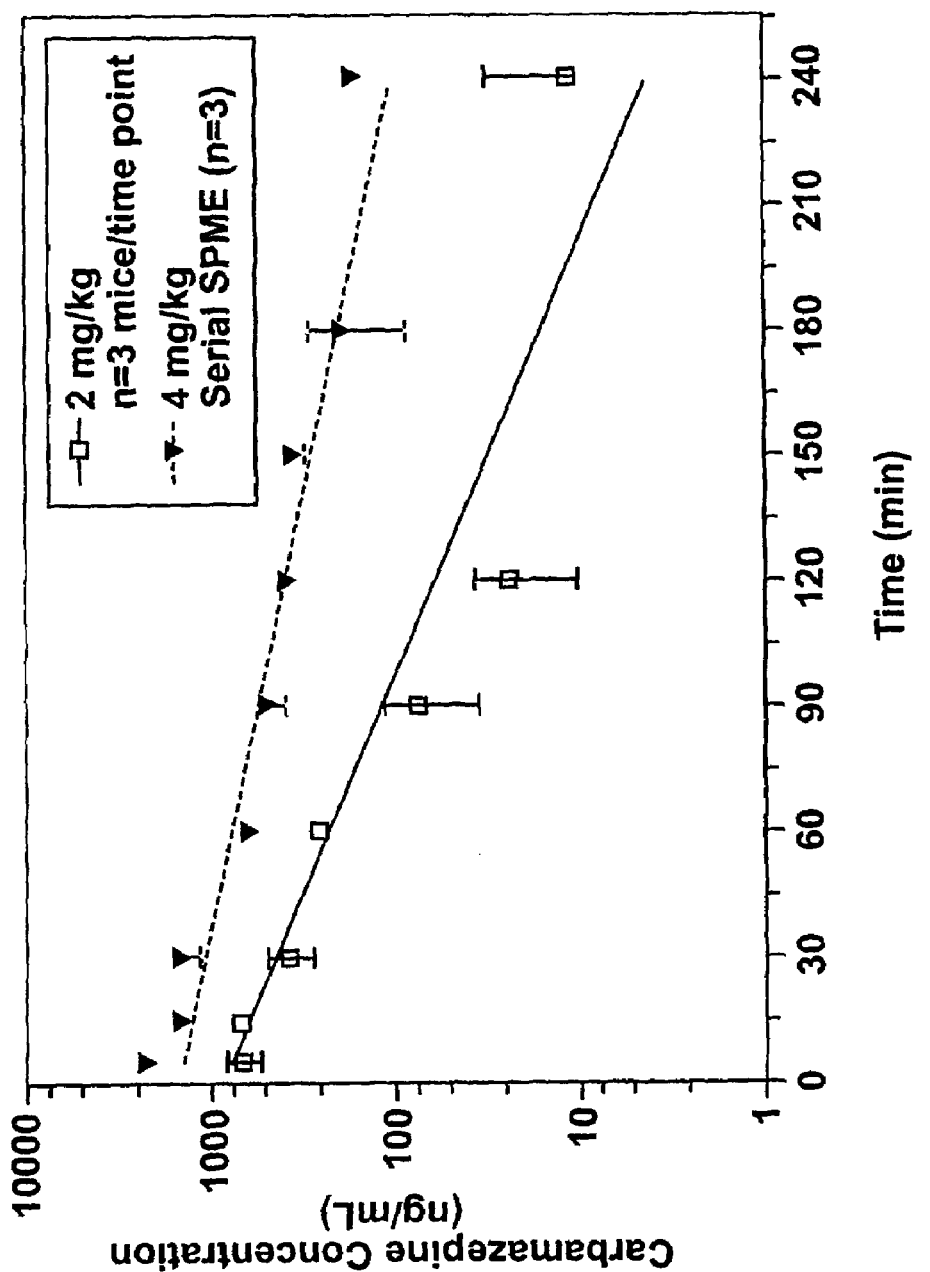
FIG. 10 is a graph of carbamazepine concentration versus time.

The mean concentration versus time profiles for carbamazepine obtained with the probes, which measure concentrations in whole blood, are compared to the results of conventional sampling and analyses in plasma in FIG. 10.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A device to extract components contained in a fluid, the device comprising:
    a housing defining a cavity, the housing having at least one opening to allow fluid flow into and out of the cavity;
    a probe insertable into the cavity of the housing; and
    a channel, the channel adapted to connect the cavity to a syringe, so that when the probe is inserted into the cavity the push/pull action of the syringe causes fluid to flow into and out of the cavity through the at least one opening and contact the probe in the cavity,
    wherein at least one of a wall that defines the cavity is a septum, and the syringe comprises a needle, the needle of the syringe is adapted to pierce the septum.

2. A device according to claim 1, wherein the probe comprises a solid phase microextraction apparatus.

3. A device according to claim 1, wherein the at least one opening comprises a catheter.

4. A device according to claim 1, wherein the at least one opening comprises a cannula.

5. A device according to claim 1, wherein the at least one opening is one opening and the fluid flows into and out of the cavity through such one opening.

6. A device according to claim 1, wherein the fluid flows into the cavity through one of said opening or channel, and the fluid flows out of the cavity through the other of said opening or channel.

7. A device according to claim 1, wherein the channel comprises a luer lock, the Luer lock adapted to connect the syringe to the channel.

8. A device according to claim 1, wherein at least one of a wall that defines the cavity is adapted to sealingly receive therethrough at least a portion of the probe.

9. A device according to claim 8, wherein said wall of the cavity comprises the septum.

10. A device according to claim 9, wherein the probe comprises a needle adapted to pierce the septum.

11. A device according to claim 1, wherein the probe comprises a needle adapted to pierce the septum.

* * * * *